United States Patent [19]

Eberhard et al.

[11] Patent Number: 5,355,309

[45] Date of Patent: Oct. 11, 1994

[54] CONE BEAM SPOTLIGHT IMAGING USING MULTI-RESOLUTION AREA DETECTOR

[75] Inventors: Jeffrey W. Eberhard; Kwok C. Tam, both of Schenectady, N.Y.

[73] Assignee: General Electric Company, Schenectady, N.Y.

[21] Appl. No.: 998,720

[22] Filed: Dec. 30, 1992

[51] Int. Cl.$^5$ .......................... G06F 15/00; A61B 6/00; G01N 23/00; G21K 1/12

[52] U.S. Cl. ........................... 364/413.15; 364/413.16; 378/19; 250/208.1

[58] Field of Search ...................... 250/332, 367, 208.1; 364/413.14, 413.15, 413.16; 378/19

[56] References Cited

U.S. PATENT DOCUMENTS

| | | | |
|---|---|---|---|
| 3,889,117 | 6/1975 | Shaw, Jr. | 250/332 |
| 3,973,128 | 8/1976 | LeMay | 378/19 |
| 4,366,576 | 12/1982 | Annis | 378/146 |
| 4,414,682 | 11/1983 | Annis et al. | 378/146 |
| 4,747,117 | 5/1988 | Albrecht et al. | 378/19 |
| 4,752,691 | 6/1988 | Hawman | 250/363.1 |
| 4,777,525 | 10/1988 | Preston, Jr. | 358/102 |
| 4,942,596 | 7/1990 | Eberhard et al. | 378/109 |
| 4,965,726 | 10/1990 | Heuscher et al. | 364/413.19 |
| 5,032,990 | 7/1991 | Eberhard | 364/413.15 |
| 5,059,800 | 10/1991 | Cueman et al. | 250/367 |
| 5,068,882 | 11/1991 | Eberhard | 378/4 |
| 5,073,910 | 12/1991 | Eberhard et al. | 378/4 |
| 5,138,642 | 8/1992 | McCroskey et al. | 378/19 |
| 5,166,961 | 11/1992 | Brunnett et al. | 378/19 |

OTHER PUBLICATIONS

"Image Reconstruction from Cone-Beam Projections: Necessary and Sufficient Conditions and Reconstruction Methods", Bruce D. Smith, IEEE Transactions on Medical Imaging, vol. MI-4, No. 1, Mar. 1985, pp. 14–25.

"Iterative Three-Dimensional Reconstruction from Twin-Cone Beam Projections", M. Schlindwein, IEEE Transations on Nuclear Science, vol. NS-25, No. 5, Oct. 1978, pp. 1135–1143.

"Cone Beam Tomography: Recent Advances and a Tutorial Review", Bruce D. Smith, Optical Engineering, May 1990, vol. 29, No. 5, pp. 524–535.

*Primary Examiner*—Roy N. Envall, Jr.
*Assistant Examiner*—Stephen R. Tkacs
*Attorney, Agent, or Firm*—David C. Goldman; Paul R. Webb, II

[57] ABSTRACT

A multi-resolution array detector includes a fine resolution zone having a higher density of detector elements than in a coarse resolution zone having a relatively lower density of detector elements. The array detector, usually an area detector, is used in computerized tomography (CT) imaging to provide a finer resolution image in one zone than in another zone. A method of processing data from the multi-resolution detector uses a nonuniform distribution of data in Radon space.

7 Claims, 5 Drawing Sheets

CONE BEAM SPOTLIGHT IMAGING USING MULTI-RESOLUTION AREA DETECTOR

CROSS REFERENCE TO RELATED APPLICATIONS

The invention disclosed and claimed herein is related to the subject matter of the following commonly-assigned patent applications, the entire disclosures of which are hereby incorporated by reference:

Ser. No. 07/631,818, filed Dec. 21, 1990, invented by Kwok C. Tam, entitled "PARALLEL PROCESSING METHOD AND APPARATUS FOR RECONSTRUCTING A THREE-DIMENSIONAL COMPUTERIZED TOMOGRAPHY (CT) IMAGE OF AN OBJECT FROM CONE BEAM PROJECTION DATA OR FROM PLANAR INTEGRAL" now abandoned;

Ser. No. 07/631,815, filed Dec. 21, 1990, pending, in the name of Kwok C. Tam, entitled "METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT" now U.S. Pat. No. 5,257,813;

Ser. No. 07/998,330, filed Dec. 30, 1992, in the name of Jeffrey W. Eberhard, Kwok C. Tam, and Kristina H. Hedengren, entitled "THREE DIMENSIONAL COMPUTERIZED TOMOGRAPHY SCANNING CONFIGURATION FOR IMAGING LARGE OBJECTS WITH SMALLER AREA DETECTORS" now U.S. Pat. No. 5,319,693; and Ser. No. 07/725,142, filed Jul. 3, 1991, in the name of Kwok C. Tam entitled "METHOD AND APPARATUS FOR ACQUIRING COMPLETE RADON DATA FOR EXACTLY RECONSTRUCTING A THREE DIMENSIONAL COMPUTERIZED TOMOGRAPHY IMAGE OF A PORTION OF AN OBJECT IRRADIATED BY A CONE BEAM SOURCE".

BACKGROUND OF THE INVENTION

The present invention relates generally to three-dimensional (3D) computerized tomography (CT). More particularly, the present invention relates to a multi-resolution area detector for such imaging and the use of such a detector in a system.

In conventional computerized tomography for both medical and industrial applications, an x-ray fan beam and a linear array detector are used. Two-dimensional (2D) imaging is achieved. While the data set may be complete and image quality is correspondingly high, only a single slice of an object is imaged at a time. When a 3D image is required, a stack of slices approach is employed. Acquiring a 3D data set one 2D slice at a time is inherently slow. Moreover, in medical applications, motion artifacts occur because adjacent slices are not imaged simultaneously. Also, dose utilization is less than optimal because the distance between slices is typically less than the x-ray collimator aperture, resulting in double exposure to many parts of the body. In 2D CT, the scanning path of the source is often a simply circular scan about the object. The linear array detector is fixed relative to the source. (Although it is usual to talk about a scan path of a source relative to the object to be imaged, it is to be appreciated that the object may be rotated or otherwise moved to provide relative motion between the object and the source.)

In a system employing true cone beam geometry for 3D imaging, a cone beam x-ray source and a 2D area detector are used. An object is scanned, preferably over a 360° angular range, either by moving the x-ray source in a scanning circle about the object or by rotating the object while the source remains stationary. In either case, the area detector is fixed relative to the source. The relative movement between the source and object which is to be imaged provides scanning in either case. Compared to the conventional 2D stack of slices approach to achieve 3D imaging, the cone beam geometry has the potential to achieve rapid 3D imaging of both medical and industrial objects with improved dose utilization.

When imaging a relatively large object using 3D CT, one must use a relatively large area detector. Since relatively large area detectors tend to have rather poor spacial resolution, the quality of image produced using such an arrangement may not be satisfactory for some purposes. The difficulty in producing relatively large area detectors having high spacial resolution at reasonable cost is at least partly a result of complexities and difficulties in providing a relatively large number of detector elements within an area detector.

If a relatively large area detector will not provide satisfactory resolution when imaging a relatively large object, a relatively small, high spacial resolution, high quality area detector may be used in order to image a region of interest. However, use of such a relatively small area detector in order to image a region of interest (which is less than the complete object) provides only incomplete data (with data corruption) such that significant artifacts are present in the images. Moreover, such techniques usually image only the region of interest. Although the region of interest is the most important part of the object being viewed, it may also be helpful to have at least some imaging of the remainder of the object.

U.S. patent application Ser. No. 07/998,330, filed Dec. 30, 1992, in the name of Jeffrey W. Eberhard, Kwok C. Tam, and Kristina H. Hedengren, entitled "THREE DIMENSIONAL COMPUTERIZED TOMOGRAPHY SCANNING CONFIGURATION FOR IMAGING LARGE OBJECTS WITH SMALLER AREA DETECTORS," now U.S. Pat. No. 5,319,693, assigned to the assignee of the present application, and hereby incorporated by reference, discloses a technique for using a relatively small, high-resolution, high-quality, area detector in order to simulate a relatively large, high-resolution, high-quality area detector. The technique allows one to image parts which are too large for the area detector.

Even if one is able to obtain high resolution CT data for a relatively large object from an area detector, such high resolution data for a relatively large object will require great demands for data processing. In other words, computer processing power and computer memory requirements will be relatively high.

Inspection of large objects with high resolution requires massive data sets and lengthy reconstruction times which limit the usefulness of such inspections. Thus, even if one is able to overcome the difficulties of imaging large objects with high resolution, data processing requirements and related factors may cause further difficulties.

OBJECTS AND SUMMARY OF THE INVENTION

Accordingly, it is a primary object of the present invention to provide improved CT imaging.

A more specific object of the present invention is to provide CT imaging of a relatively large object with the benefits of high resolution, but avoiding or minimizing the disadvantages of high resolution.

A further object of the present invention is to provide CT imaging with high or good spatial resolution in a particular region of interest of an object and coarser resolution over the remainder of the object.

Yet another object of the present invention is to provide an area detector having high or fine resolution where necessary, but without the cost and complexity of relatively high numbers of detector elements.

A still further object of the present invention is to provide a system and method for high resolution imaging where it is necessary, but without requiring the excessive data processing power and memory requirements common to high resolution detectors.

The above and other objects of the present invention which will become more apparent as the description proceeds are realized by a computerized tomography two-dimensional array detector. The detector includes a fine resolution area having a density df of first detector elements and a coarse resolution area having a density dc of second detector elements. Each of the second detector elements has a larger surface area than a surface area of each of the first detector elements. The density dc is less than the density df. Each of the first and second detector elements includes a scintillator and a corresponding light sensor. Each scintillator converts x-ray energy to light. Each light sensor is a CCD. Each of the second detector elements may include a plurality of CCDs with coupled outputs. The array detector may be combined with a source of imaging energy for applying imaging energy to an object such that imaging energy passes to the array detector, a scanning means to scan the source relative to the object (may move the source with the object stationary or move the object with the source stationary), a data acquisition means connected to the array detector for acquiring multi-resolution sensed data from the array detector, a data processor connected to the data acquisition means for providing multi-resolution image data from the multi-resolution sensed data, and a display connected to the data processor for displaying multi-resolution CT images based on the multi-resolution image data.

The system according to the present invention is a computerized tomography system including a multi-resolution array detector having a fine resolution zone with a density df of first detector elements and a coarse resolution zone with a density dc of second detector element. Each of the second detector elements has a larger surface than a surface of each of the first detector elements. The density dc is less than the density df. The system further includes a source of imaging energy for applying imaging energy to an object such that the imaging energy passes to the array detector, a scanning means to scan the source relative to the object, a data acquisition means connected to the array detector for acquiring multi-resolution sensed data from the array detector, a data processor connected to the data acquisition means for providing multi-resolution image data from the multi-resolution sensed data, and a display connected to the data processor for displaying multi-resolution CT images based on the multi-resolution image data. The array detector is preferably a two-dimensional array detector. The data processor includes a means for calculating Radon derivative data at a plurality of fine resolution points in Radon space and at a plurality of coarse resolution points in Radon space, a means for obtaining Radon data for the fine and coarse resolution points, and a means for inverting the Radon data to provide the multi-resolution image data. The means for calculating and the means for obtaining each uses weighted integration.

The method of the present invention is a method of computerized tomography including applying imaging energy from a source to at least a region of interest including a spotlight region of an object. The source is moved relative to the object in a data scan path (either the source or the object is moved as long as there is relative motion between them). Multi-resolution sensed data is acquired representative of the region of interest using a multi-resolution array detector as described above. The multi-resolution sensed data has a higher density relative to the spotlight region than outside of the spotlight region. The multi-resolution sensed data is converted to multi-resolution image data. An image of the region of interest based on the multi-resolution image data is displayed and the image has a higher resolution relative to the spotlight region than outside of the spotlight region. The array detector is preferably an area detector and three-dimensional computerized tomography is performed in the method. The converting step includes substeps of calculating Radon derivative data at a plurality of fine resolution points in Radon space and at a plurality of coarse resolution points in Radon space, obtaining Radon data for the fine and coarse resolution points, and inverting the Radon data to provide the multi-resolution image data. The calculating and obtaining substeps use weighted integration.

BRIEF DESCRIPTION OF THE DRAWINGS

The above and other features of the present invention will be more readily understood when the following detailed description is considered in conjunction with the accompanying drawings wherein like characters represent like parts throughout the several views and in which.

DETAILED DESCRIPTION

Figure 1:
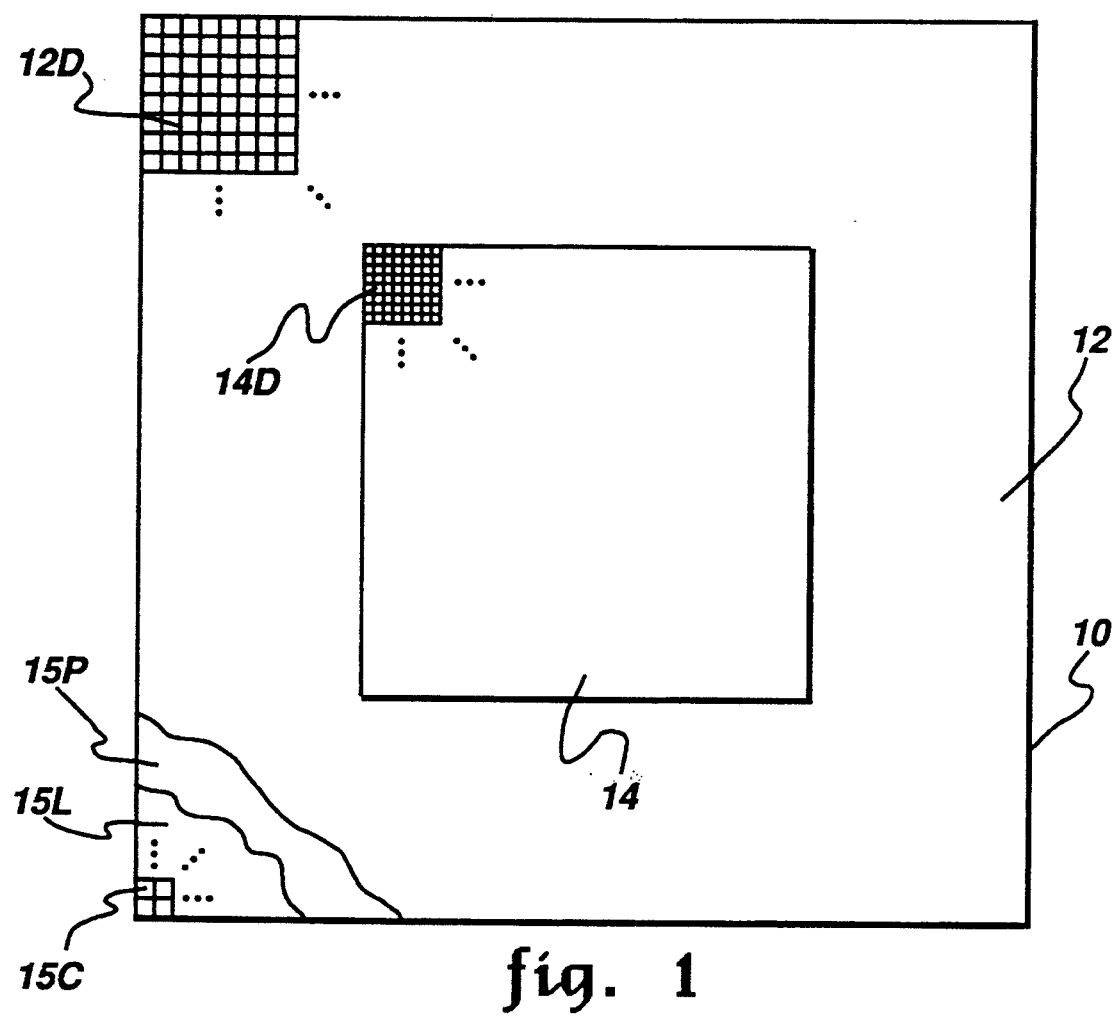
FIG. 1 is a simplified planar view of an area detector according to the present invention with partial layers broken away.

With reference now to FIG. 1, an area detector 10 according to the present invention will be discussed. The area detector 10 includes an outer zone 12 which extends around a square inner zone 14. The outer zone or area 12 has medium resolution, whereas the inner zone or area 14 has high resolution. The relatively fine resolution of zone 14 is obtained by having a significantly higher density df of detector elements 14D in zone 14 as compared with the more coarse resolution associated with the lower density dc of detector elements 12D within the outer zone 12. Each of the detector elements 14D would be significantly smaller in size than the detector elements 12D in zone 12. For ease of illustration, only a relatively small number of detector elements 14D are shown in the zone 14, but it will be appreciated that the detector elements 14D are distributed throughout the zone or area 14. Likewise, only a relatively small number of detector elements 12D are shown in the zone 12, but such detector elements would be distributed throughout the area or zone 12 which extends, similar to a picture frame, around the inner zone 14. Preferably, the density of detector elements 14D is uniform within zone 14 and the density of detector elements 12D is uniform throughout area 12.

An example of construction specifics for an area detector 10 according to the present invention will be given. The area detector 10 might, for example, be a square with 12 inches on its sides. The outer zone 12 may have 600 detector elements 12D along each of its outer edges, each detector element 12D being a square of dimensions 0.020 inches by 0.020 inches. If that density for the detector elements 12D was maintained throughout the area of area detector 10, the area detector would have 360,000 (600 by 600) detector elements. However, the inner zone 14, which for this example would be a six inch square, does not include any of the detector elements 12D. Accordingly, the area detector 10 includes only 270,000 detector elements 12D. However, the inner zone 14 may include 600 by 600 detector elements 14D for a total of 360,000 detector elements 14D, each being square with a size of 0.010 inches by 0.010 inches. Accordingly, the area detector 10 includes 270,000 of the larger detector elements 12D and 360,000 of the smaller detector elements 14D for a total number of detector elements of 630,000. For comparison purposes, an area detector having the same size and having the higher resolution throughout (i.e., detector elements of the size of elements 14D throughout) would require 1,440,000 detector elements. In addition to cost and complexity problems in making such a large, high resolution area detector, such an area detector with over one million detector elements would generate that much more data and require corresponding increases in data processing power and/or increases in reconstruction time. Further, the large amount of data generated may require increased memory capacity.

The area detector 10 may be constructed using known techniques. A brief description of a type of area detector 10 utilizing the principle illustrated in FIG. 1 will be presented. The area detector 10 may have slabs of scintillator on top of photo-sensitive elements such as charged couple device (CCD) arrays. However, instead of dicing the scintillator into elements of uniform size as previously done, the present invention would have the scintillator diced into elements of one size in a lower resolution area such as 12 in FIG. 1, and diced into elements of a smaller size in a high resolution area such as 14 of FIG. 1. The dicing is simply a cutting using a saw so as to effectively establish a boundary (then filled in with light reflective material) between different portions of the scintillator. The output light from the scintillator with coarse dicing in one area and fine dicing in another area would be directed into a CCD array (layer 15L with CCDs 15C) using lenses (part of intermediate layer 15P) or other known coupling technique.

The actual construction of the area detector 10 may utilize the techniques disclosed in U.S. Pat. No. 5,059,800, entitled "TWO DIMENSIONAL MOSAIC SCINTILLATION DETECTOR," issued Oct. 22, 1991 to Michael K. Cueman, Gregory A. Mohr, and Dale M. Brown, assigned to the assignee of the present application, and hereby incorporated by reference. However, the area detector 10 would be different from that prior patent in that it would have a non-uniform density of the detectors. Therefore, the scintillator block or slab would be cut into smaller blocks within area 14 and larger blocks within area 12. As discussed in the prior patent, such different sized scintillator blocks would be optically coupled to a corresponding CCD of a CCD array. Accordingly, any light produced from an x-ray passing through one of the blocks of scintillation material will be supplied to a corresponding CCD. One could use non-uniform size CCDs corresponding on a one-to-one basis with each of the scintillator blocks, each of the scintillator blocks, corresponding CCD and optical coupling between the scintillator block and CCD collectively constituting a detector element. Alternately, a uniform density CCD array could be used in conjunction with the non-uniform density of scintillation blocks with a one-to-one correspondence between scintillation blocks and CCDs in area 14 and a one-to-four correspondence between scintillation blocks and CCDs in area 12. In that case, the CCDs in the area 12 would have four adjacent CCDs coupled together to effectively function as a single CCD. In other words, an x-ray falling upon a scintillation block corresponding to one of the detector elements 12D would generate light which would be coupled (possibly using a lens or other optical arrangement) to one or more of the four CCDs corresponding to that scintillation block. Since the output signals of all four CCDs corresponding to a particular scintillation block are coupled together, one has effectively simulated a larger CCD. Note that the ratio between the large scintillation blocks and the corresponding CCDs would not necessarily be four, but would usually be based upon the ratio of surface area of detector elements 12D to detector 14D. As used herein, the surface area of a detector element is the area upon which imaging energy may hit the detector element. Thus, one can make the multi-resolution area detector 10 by simply dicing (cutting) the original scintillation slab into non-uniform size blocks while using uniform size CCDs or by using the non-uniform size scintillation blocks together with non-uniform size CCDs. In either case, the construction details may be accomplished in generally known fashion and may, for example, use the techniques described in the incorporated by reference Cueman et al patent.

The two-zone or multi-resolution area detector 10 can be used in several different fashions. First, for small parts which can be spanned entirely within the high resolution zone 14, the detector can simply be used to image the small part directly at high resolution. For large parts where there is no need for high resolution, the high resolution detector elements 14D in the zone 14 can simply be coupled together to provide uniform resolution throughout area detector 10. Referring back to the example having specific dimensions, coupling four of the 0.010 inch by 0.010 inch detector elements provides the equivalent to the 0.020 inch by 0.020 inch square detector elements. The detector elements 14D may be coupled together by simply adding the signals from four adjacent detector elements 14D in order to synthesize a single larger detector element.

Most importantly, the detector 10 may be used in what will be referred to as a spotlight mode to create an image with a high resolution spotlight zone and a lower resolution zone. This imaging mode provides high quality information about a portion of the object being viewed and provides lower resolution information about the remaining material. In this way, a particular zone of the object can be emphasized in the inspection, but without giving up information about adjacent parts of the object. The collection of high resolution data in only a sub-volume of the object substantially reduces system complexity. The amount of data collected is significantly reduced since it is now unnecessary to collect high resolution data over the entire part. This, in turn, reduces the computational complexity in essentially all the subsequent imaging steps including preprocessing, 3D image reconstruction, and 3D image processing and analysis. Reduced system complexity in turn results in higher throughput and lower cost.

Most manufactured parts have zones where flaws are more critical to life than in other sections of the part (e.g., high stress regions, regions where cooling of the casting is more difficult, etc.) The present use of a multi-resolution area detector 10 provides high quality inspection in the particular region or regions where high performance inspection is most critical. For high volume parts, custom detectors could be designed to arrange the location of the high resolution region as appropriate for that specific part. In particular, the high resolution region need not be at the center of the detector, but can be positioned as desired to make the inspection feasible. Although area detector 10 has been shown as having two different resolution areas, one could have three or more different zones, each zone having a different element size for different resolution.

Figure 2:
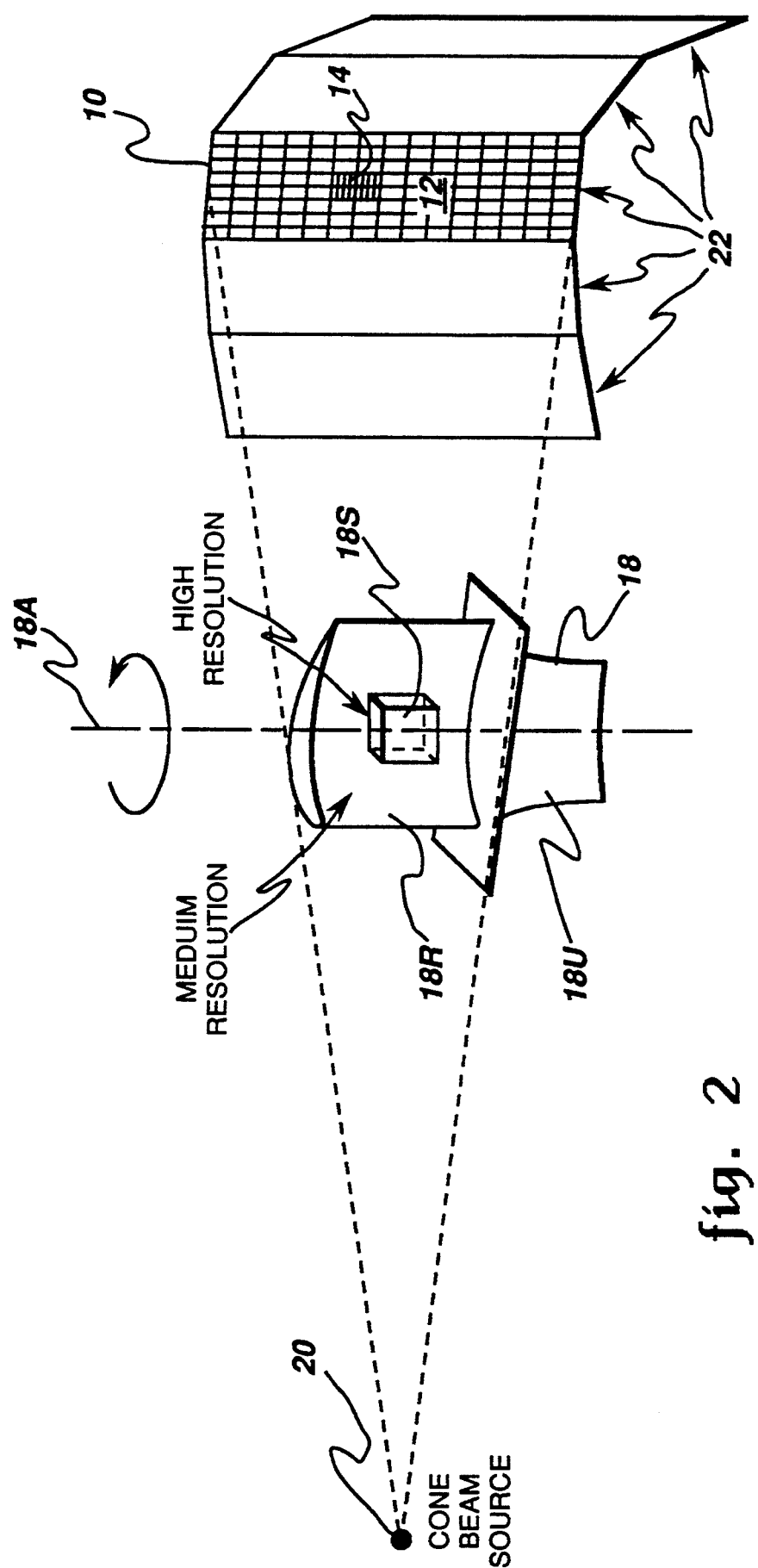
FIG. 2 is a simplified perspective view illustrating the use of the area detector in an imaging system.

With reference now to FIG. 2, the area detector 10 is used in order to image a portion 18R of an object 18 using a source 20. Although shown as a turbine blade, the object 18 could be any work piece, part of a medical patient, or any other object which is to be imaged. The object 18 is rotated about its central axis 18A in order to provide scanning movement relative to source 20 and area detector 10. Alternately, and equivalently, the source 20 and area detector 10 could be rotated about axis 18A while the object 18 is maintained stationary. In either case, this would be considered a circular scan. However, the scanning path could be more complex than a simple circular scan.

Ideally, the object 18 would fit entirely within the height and width of the area detector 10. In other words, any ray from source 20 passing through the object 18 would necessarily strike one of the detector elements in area detector 10. However, FIG. 2 has been drawn to illustrate that the area detector 10 may be used to image a portion 18R of object 18 while another portion 18U is not imaged. Further, in addition to not imaging portion 18U because it extends below the height of area detector 10, FIG. 2 illustrates how the high resolution zone 14 corresponds to a region 18S which is being called the spotlight region. That spotlight region is the region within portion 18R which is imaged with high resolution.

FIG. 2 further illustrates that, in cases where the region to be imaged 18R extends in width such that it cannot be spanned by the area detector 10, the area detector 10 may be used to simulate an area detector having five panels including the location shown for area detector 10 together with the four panels 22. In other words, each of the panels 22 corresponds to area detector 10 having been moved to a different location in order to simulate a five panel area detector using techniques described in detail in the incorporated by reference U.S. patent application Ser. No. 07/998,330, now U.S. Pat. No. 5,319,693.

Having described the multi-resolution area detector 10 according to the present invention, various known techniques can be used for imaging data based upon imaging energy sensed by the area detector 10. However, the present invention includes a specific imaging technique which maximizes the advantages from use of a multi-resolution area detector. The technique, which will be described below, modifies existing techniques of imaging in such a way as to most efficiently process the data. This allows one to reduce the data processing power required and the data memory storage requirements.

Figure 3:
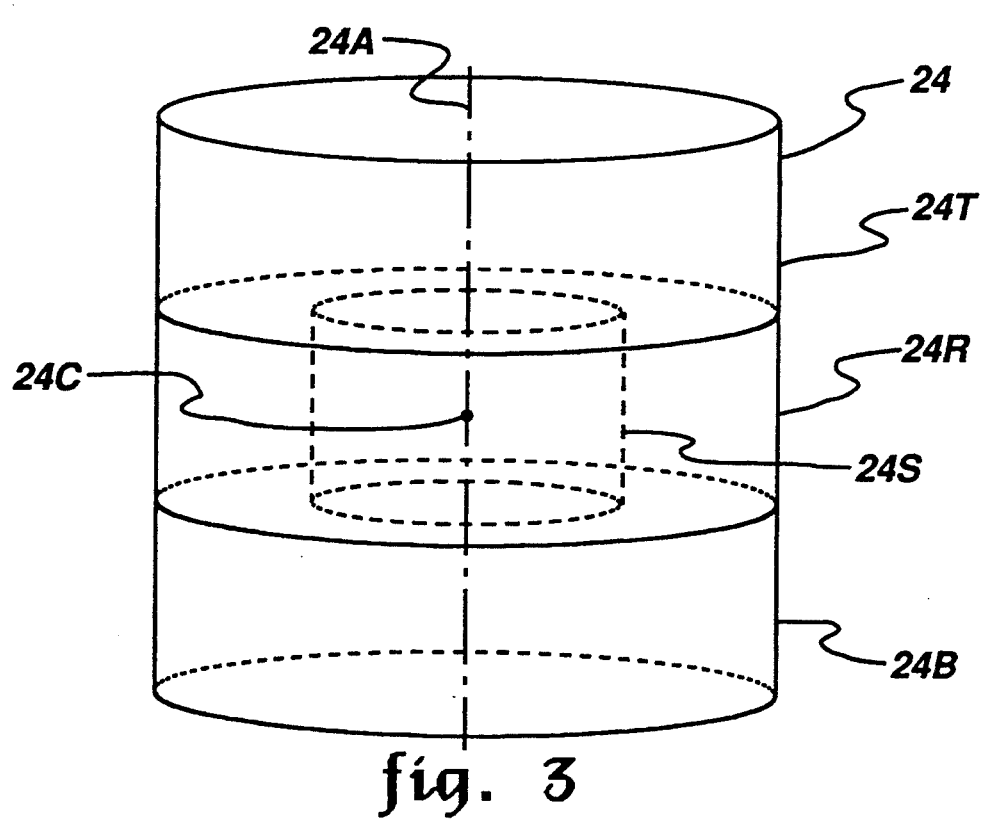
FIG. 3 is a perspective view of an object which is to be imaged.

FIG. 3 shows an object 24 which is to be imaged. The object 24 is shown as a cylinder having a generally cylindrical region of interest 24R disposed between a top cylindrical region 24T and a bottom cylindrical region 24B. Within the region of interest 24R is a centrally located spotlight region 24S. In particular, the region 24S is the region for which a fine resolution image is required.

Figure 4:
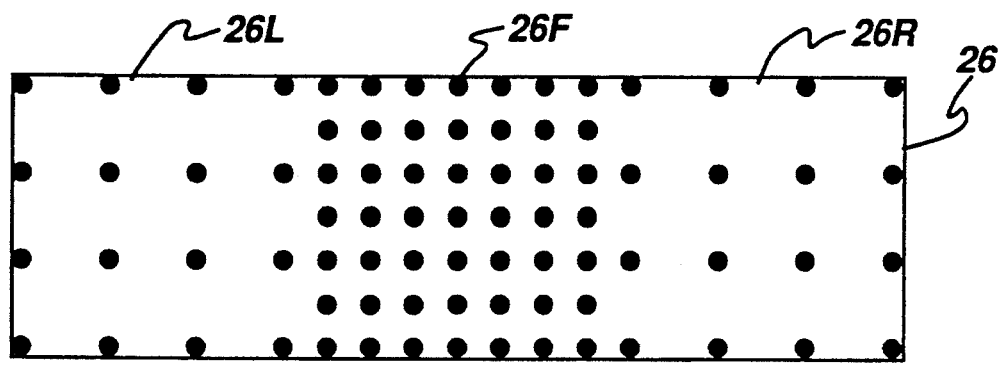
FIG. 4 is a schematic representation of an area detector according to the present invention.

In order to image the region of interest 24R with region 24S being spotlighted (i.e., imaged at a higher resolution), the hybrid detector 26 of FIG. 4 may be used. The area detector 26 is illustrated in schematic form only as having a fine resolution area 26F having a higher density of detector elements than coarse resolution areas or zones 26L and 26R disposed at left and right sides. The detector 26 and its elements would be constructed in the same fashion as discussed above with respect to FIG. 1. Alternately, the area detector 26 may simply be three different area detectors (not shown) with a fine resolution area detector disposed in between two coarse resolution area detectors.

The hybrid detector 26 of FIG. 4 might be used for 3D CT imaging in the same fashion as described in more detail in the incorporated by reference U.S. patent applications Ser. Nos. 07/631,815, now U.S. Pat. No. 5,257,813, and 07/631,818, now abandoned. The first of these two applications describes, among other things, a technique for computing Radon derivative data and integrating the Radon derivative data to get Radon data on a polar grid. The second of these two applications describes a technique for inverting the Radon data to provide a 3D reconstructed image in the object space. Although the techniques of those two prior applications may be used in conjunction with the hybrid detector 26 of FIG. 4 (as well as the hybrid or multi-resolution detector 10 of FIG. 1), this would not allow one to fully obtain the reductions in computational power requirements and memory requirements. Such a direct use of those prior techniques would require one to have a uniform density of points in Radon space. Accordingly, the present invention includes a technique for modifying the prior techniques of those two applications in order to take full advantage of the reduced computational or data handling requirements and the reduced memory requirements arising from use of a multi-resolution area detection. Since the present technique relies upon modifications of the techniques disclosed in those two prior applications, the differences between the present technique and those prior techniques will be emphasized and it is not necessary to repeat those details of the prior techniques which are common to the present technique.

In order to best use the detector 26 of FIG. 4 for imaging the object 24 of FIG. 3, the spotlight region 24S should be centrally located relative to a rotation axis 24A. As discussed with respect to axis 18A of FIG. 2, the rotation axis 24A is the axis about which object 24 will be rotated relative to a source and detector (not shown in FIG. 3) or about which the source and detector would be rotated relative to the object 24. Rotation of the source and detector together is equivalent to rotating the object since the relative motion is the same in each case. In addition to locating the rotation axis 24 so that it passes through the spotlight region 24S, the origin of Radon space should be located near the center of the spotlight region 24S. Although the location of the origin of the Radon space at the center 24C of spotlight region 24S is not absolutely necessary, this is highly advantageous in minimizing computational or data processing power requirements and/or memory requirements. This geometry allows the support of the spotlight region 24S to be held to a minimum size. The support of the spotlight region is that zone within Radon space which defines the spotlight region. By minimizing the size of that support within Radon space, the efficiency of the present technique is maximized.

Figure 5:
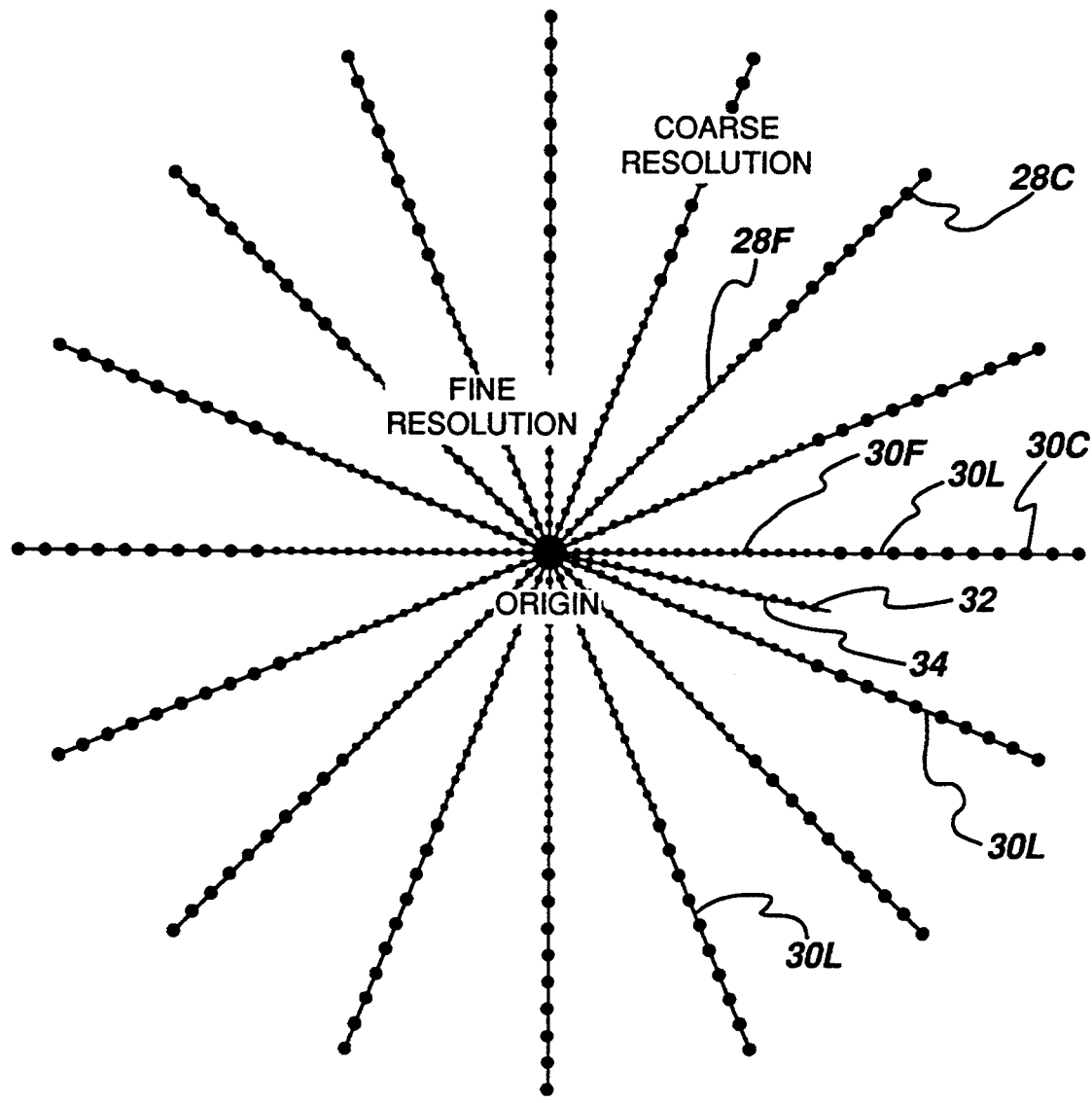
FIG. 5 is a hybrid polar grid in Radon space.

Turning now to FIG. 5, a vertical plane in Radon space is shown having a hybrid polar grid. In particular, this data set is like that shown in the bottom of FIG. 4 of U.S. patent application Ser. No. 07/631,815, now U.S. Pat. No. 5,257,813, and shown in the lower left of FIG. 4 in U.S. patent application Ser. No. 07/631,818, now abandoned. FIG. 3 and the associated text of each of those two applications defines the 3D Radon transform of an object at a given point. As shown in present FIG. 5, the hybrid polar grid established in Radon space includes a fine resolution zone 28F in a central, circular area around the origin and a coarse resolution area 28C extending like a circle around the fine resolution area 28F. The Radon space includes high density points 30F in zone 28F, which points are in line with the lower density or coarse resolution points 30C in the region 28C extending like a ring around the region 28F. In addition to the points 30F which are in line with the points 30C, the fine resolution area 28F may include high density or fine resolution points 32 extending on lines 34 which do not pass out of region 28F. For ease of illustration, only a single such line 34 is shown between two of the lines 30L upon which points 30F and 30C are located. However, it will be appreciated that one or more such lines may be disposed in between each of the adjacent of the lines 30L. For ease of illustration, not all of the lines 30L have been labeled and, likewise, not all of the points have been labeled. Each of the points 30F, 30C, and 32 is a point at which the Radon derivative data has been calculated using the techniques described in the incorporated by reference applications Ser. Nos. 07/631,815, now U.S. Pat. No. 5,257,813, and 07/631,818, now abandoned. The spacing between adjacent ones of the coarse points 30C is dependent upon the spacing between adjacent detector elements in the coarse resolution areas of area detector 26 in FIG. 4 in known fashion. Likewise, and also based upon prior known relationships between density of points used in Radon space and density of detector elements from the area detector, the fine resolution data points 30F and 32 will have a density and spacing based upon the density of detector elements within the fine resolution area 26F of the area detector 26. Finally, the size of the fine resolution area 28F is the minimum size necessary to be the support of the spotlight region 24S. This support is the zone in Radon space which can completely define the spotlight region 24S.

Thus, FIG. 5 shows a polar grid in Radon space similar to that of the two last-mentioned applications except that there is a non-uniform density of points at which Radon derivative data has been calculated. Instead of having a uniform density as with the two last-mentioned applications, Radon derivative data is calculated at a higher density in the fine resolution zone 28F in Radon space and is calculated at a lower density in the coarse resolution zone 28C in Radon space. This technique will advantageously reduce computational power requirements and memory requirements as compared with using the hybrid or multi-resolution area detector 26 of FIG. 4 in conjunction with uniformly spaced (i.e., fine resolution) data points in Radon space.

The Radon derivative data on the hybrid Radon polar grid points 30C and at the fine points 30F and 32, is calculated by doing weighted line integration on the cone beam projection image using the method described in detail in the incorporated by reference U.S. patent application Ser. No. 07/631,815, now U.S. Pat. No. 5,257,813. The difference in calculation in the present invention and in that prior patent application is that the prior application had uniform density of points such that the line integration was uniformly weighted (or it might be said to be unweighted). However, with the present technique, the line integration should be weighted according to the spacing between data points. For example, if the separation distance between the coarse points 30C is twice the separation distance between the fine points 30F and 32, a weighted line integral along a line including a fine point and a coarse point will multiply that contribution from the coarse point by two, whereas the contribution from the fine point would not be multiplied by anything (i.e., equivalent to multiplying by a weight of one).

Figure 6:
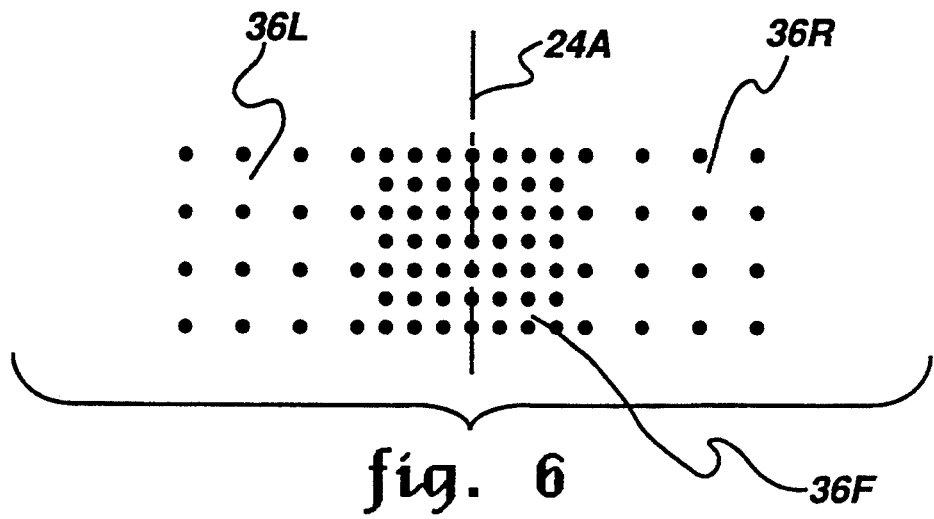
FIG. 6 is a hybrid Cartesian grid of the reconstructed image on vertical planes in the first step of fast Radon inversion.

Once the Radon derivative data on the hybrid polar grid shown in FIG. 5 and on other hybrid polar grids (not shown but calculated in the same fashion) and in accord with the general techniques described by the two last-mentioned incorporated by reference U.S. patent applications, the Radon derivative data on each polar grid line 30L and 34 would be integrated in order to get the Radon data for that grid line with hybrid resolution. The integration would use the same techniques as described in the last two U.S. patent applications except that the integration would again be weighted. Once the Radon data for each of the points 30C, 30F, and 32 is obtained, it is then necessary to invert the Radon data on the hybrid polar grid in the Radon space to yield a 3D reconstructed image in hybrid Cartesian grid in the object space with fine resolution in the spotlight region 24S and coarse resolution elsewhere. The Radon inversion can be achieved, for example, using the fast Radon inversion method disclosed in U.S. patent application Ser. No. 07/631,818 except that weighted integrations would be used where fine and coarse data is integrated. In particular, the techniques of that prior application are used to generate a projection of the reconstructed image on vertical planes in the first step of the fast Radon inversion. The vertical planes would correspond to the vertical planes such as the vertical plane of FIG. 5, it being understood from the two last-mentioned applications that FIG. 5 is one of numerous vertical planes. The projection of the reconstructed image on vertical planes corresponds to the hybrid or multi-resolution Cartesian grid of the reconstructed image on a vertical plane as shown in FIG. 6. That is, FIG. 6 shows the point density for projections of image on a vertical plane. The axis 24A has been drawn into FIG. 6 in order to show the correspondence between the point density for the projection of the reconstructed image on the vertical plane and the object 24 of FIG. 3. The grid of FIG. 6 includes a central fine resolution or high density zone 36F and two low resolution or low density zones 36L and 36R.

Figure 7:
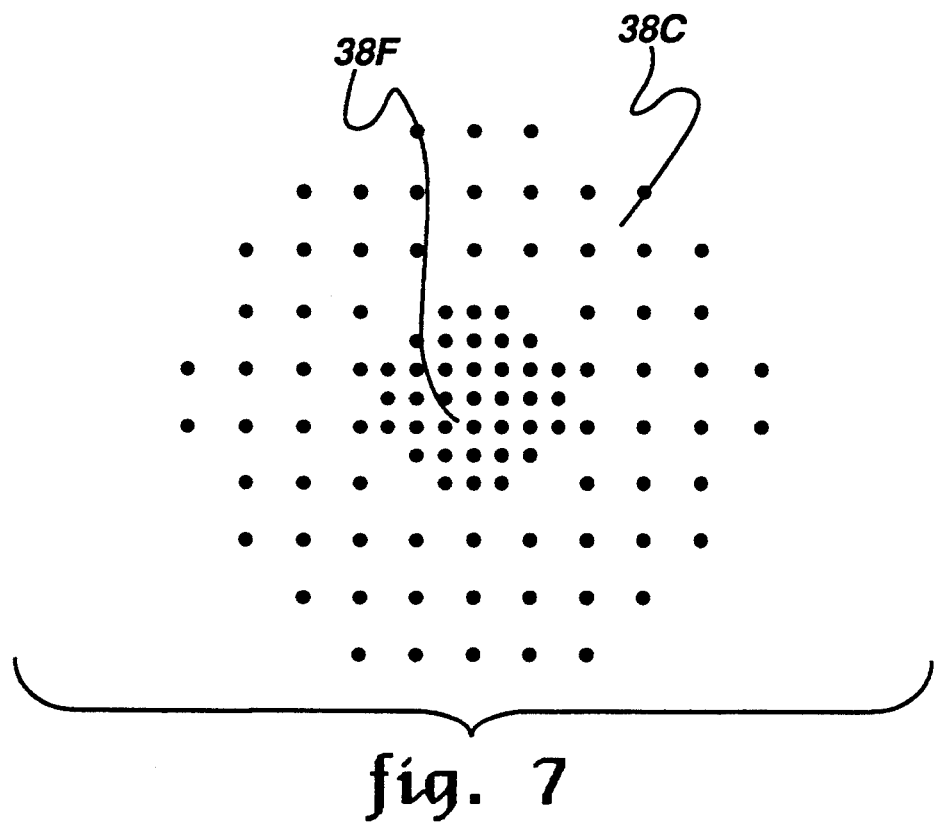
FIG. 7 is a hybrid Cartesian grid of the reconstructed image on horizontal planes in the second step of fast Radon inversion.

Proceeding from the grid of FIG. 6 and numerous similar grids corresponding to different vertical planes, the second step of fast Radon inversion from U.S. patent application Ser. No. 07/631,818, now abandoned, may be accomplished in order to generate a reconstructed image on horizontal planes. FIG. 7 is a hybrid Cartesian grid simply illustrating that the point density of the reconstructed image on a horizontal plane would vary between a central high density or fine resolution zone 38F and a coarse resolution or low density zone 38C. Accordingly, the multi-resolution detector 26 of FIG. 4 may be used to reconstruct an image of region of interest 24R (FIG. 3) with the image of spotlight region 24S having higher resolution than the remainder.

Figure 8:
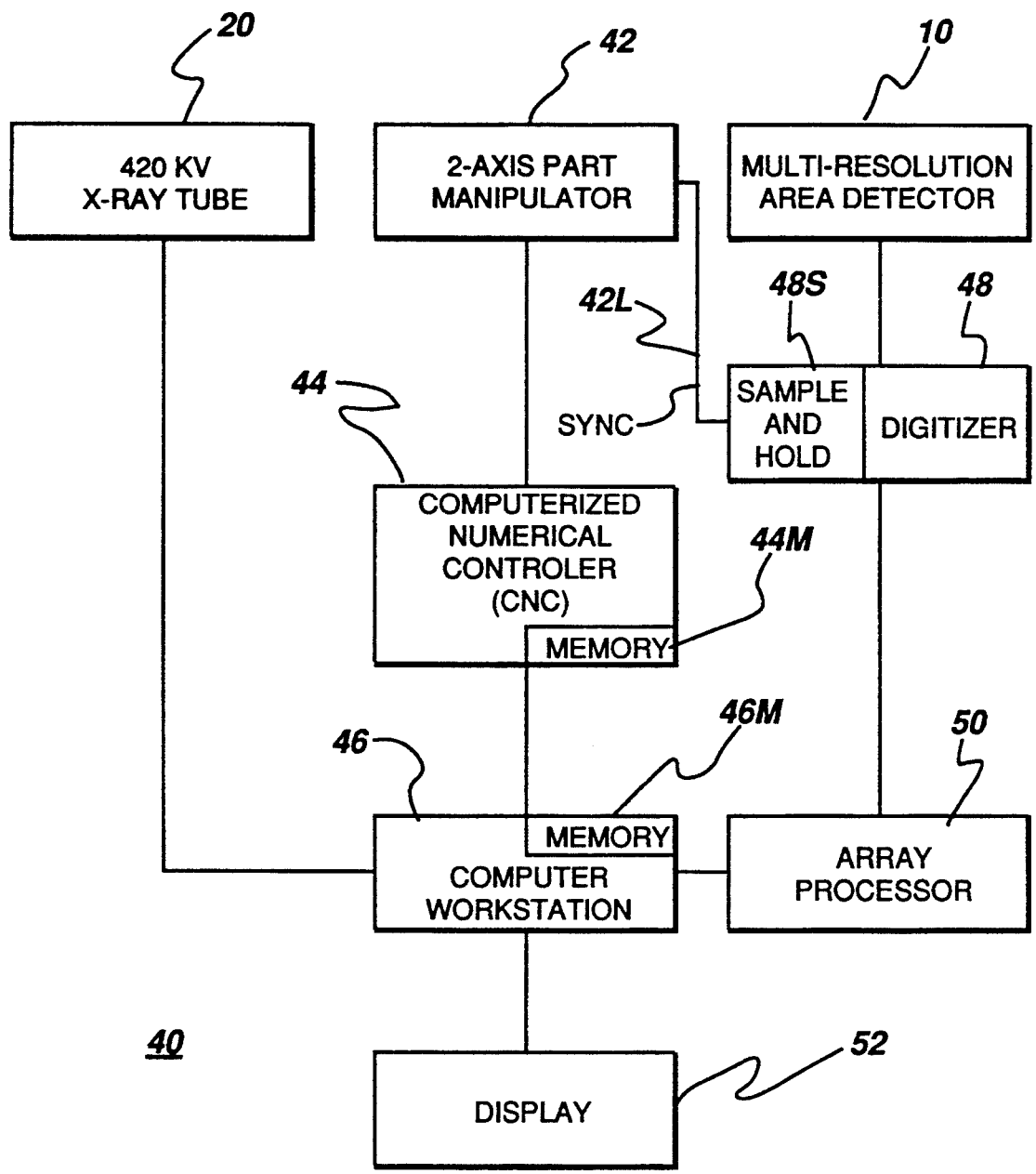
FIG. 8 is a block diagram of the system of the present invention.

Turning now to FIG. 8, a system 40 according to the present invention will be discussed. The system 40 includes the multi-resolution area detector 10 (could alternately be multi-resolution or hybrid detector 26) and a source 20. Although the source 20 has been shown as an x-ray tube, the cone beam source 20 could alternately provide neutrons, positrons, or other forms of radiation or electromagnetic energy from a point source. Alternately, other forms of imaging energy might be used.

A manipulator 42, which may be a two-axis part manipulator, is used to provide relative scanning between the object (not shown in FIG. 8) being imaged and the source 20. Although the manipulator 42 is designed to move the object, the manipulator 42 might alternately move the source 20 and area detector 10 in unison.

The manipulator 42 is controlled by a known computerized numerical controller 44, which may, for example, be a type made by Aerotech. The controller 44 may include a memory 44M having data defining various scan paths in known fashion. Alternately, and also using well known techniques, a memory 46M of a computer work station 46, which is connected to the controller 44, may have the data which defines movements of the manipulator 42 and therefore defines the scan path or trajectory. The computer work station 46 may be a brand of work station made by Sun, although other computer work stations and possibly even personal computers might be used in place of the work station. The computer work station controls the other components of the system 40 in known fashion.

Connected to the area detector 10 is a digitizer 48 which operates in known fashion to convert analog signals from the area detector into digital signals representative of the image of the object under test. The digitizer 48 may include sample and hold circuits 48S operating in response to a synch signal on line 42L in known fashion.

The digitized values corresponding to the sensed radiation from the detector elements within the detector 14 are supplied from the digitizer 48 to a data array processor 50. The array processor 50, which may be of a known commercially available type such as a Meiko M40, provides the necessary signal processing for the signals coming from the digitizer 48. The array processor 50 may perform the necessary image processing such that a display might be connected directly to the array processor to display the images from the CT scan. However, in the arrangement shown in FIG. 8, the processed data from array processor 50 is supplied to a computer work station 46 and the computer work station 46 in turn supplies the data, with or without further processing, to a display 52 which displays the CT images.

The memory 46M includes a computer program having a portion serving as a means to calculate the Radon derivative data in a non-uniform point density such as shown for FIG. 5. Additionally, a portion of the program will serve as a means for computing the Radon data from the Radon derivative data by a weighted integration along the polar grid lines. Finally, the computer program will include a portion serving as a means for performing the fast Radon inversion two step method as discussed above.

The array processor 50 and/or computer 46 function as a data processor for converting multi-resolution sensed data from area detector 14 into multi-resolution image data for display on the display 52. In the usual case of the present invention where the detector elements 12D (FIG. 1 only) have a different surface area than detector elements 14D, the signals from elements 12D may be scaled or normalized to take into account differences in surface area relative to signals from elements 14D. The multi-resolution sensed data has a higher density relative to the spotlight region of the object being viewed than it has outside of the spotlight region. Likewise, the multi-resolution image data has a higher density corresponding to the spotlight region. A computer program within a memory of array processor 50 (or possibly within memory 46M) includes a portion serving as a means for calculating Radon derivative data at a plurality of fine resolution points in Radon space and at a plurality of coarse resolution points in Radon space using the technique discussed above. Further, the program within memory 46M includes a portion serving as a means for obtaining Radon data for the fine and coarse resolution points and a portion serving as a means for inverting the Radon data to provide the multi-resolution image data. The means for calculating the Radon derivative data and the means for obtaining Radon data use weighted integration in the fashion as discussed above.

Although the present discussion has focused upon an area detector as the multi-resolution array detector, it shall be appreciated that the present invention has applicability to a linear or one dimensional array detector. For such a multi-resolution linear or line array detector, a single row (or single column) of detector elements would have a higher density in one zone than in another zone. Generally, such a detector (not shown) could be used for two dimensional CT imaging.

Although various specific constructions have been given for the present invention, it is to be understood that these are for illustrative purposes only. Various modifications and adaptations will be readily apparent to those of skill in the art. For example, although the present invention has been described with reference to a source which physically moves relative to the object during the scanning operation, an alternative is possible. In such an alternative, a material may be around or partially around the object to be viewed, which material generates imaging energy upon being struck by a different kind of energy beam. The beam applied to the source material causes the source material to in turn emit an imaging energy. Although the source is not physically moved relative to the object, the source would effectively be moved relative to the object by sweeping the beam striking the source material in a path corresponding to the trajectory. In similar fashion and as used herein, moving the source relative to the object shall include situations where a series of sources are turned on sequentially to effectively move the source as well as the beam striking a source material type of source movement. In view of these and other modifications, the scope of the present invention should be determined by reference to the claims appended hereto.

What is claimed is:

1. A computerized tomography system comprising:
    a multi-resolution array detector having a fine resolution zone with a density df of first detector elements and a coarse resolution zone with a density dc of second detector elements, and said density dc being less than said density df;
    a source of imaging energy for applying imaging energy to at least a region of interest including a spotlight region of an object such that imaging energy passes to said array detector;
    scanning means to move said source relative to the object about a rotation axis substantially centered with respect to said spotlight region;
    data acquisition means connected to said array detector for acquiring multi-resolution sensed data from said array detector;
    a data processor connected to said data acquisition means for providing multi-resolution image data from said multi-resolution sensed data, said data processor including means for calculating Radon derivative data at a plurality of fine resolution points in Radon space and at a plurality of coarse resolution points in Radon space, said data processor further including means for obtaining Radon data for the fine and coarse resolution points and means for inverting the Radon data to provide the multi-resolution image data;
    said means for calculating and said means for obtaining each using weighted integration; and
    a display connected to said data processor for displaying multi-resolution CT images based on said multi-resolution image data.

2. The computerized tomography system of claim 1 wherein each of said first and second detector elements includes a scintillator and a corresponding light sensor.

3. The computerized tomography system of claim 2 wherein each scintillator converts x-ray energy to light.

4. The computerized tomography system of claim 3 wherein each light sensor is a CCD.

5. The computerized tomography system of claim 1 wherein said array detector is a two-dimensional array detector and each of said second detector elements has a larger surface area than a surface area of each of said first detector elements.

6. A method of computerized tomography comprising the steps of:
    applying imaging energy from a source to at least a region of interest including a spotlight region of an object;
    moving the source relative to the object about a rotation axis substantially centered with respect to said spotlight region in a data scan path;
    acquiring multi-resolution sensed data representative of the region of interest using a multi-resolution two-dimensional array detector having a fine resolution zone with a density df of first detector elements and a coarse resolution zone with a density dc of second detector elements, and said density dc being less than said density df, said multi-resolution sensed data having a higher density relative to the spotlight region than outside of the spotlight region;
    converting the multi-resolution sensed data to multi-resolution image data, said converting step including the substeps of calculating Radon derivative data at a plurality of fine resolution points in Radon space and at a plurality of coarse resolution points in Radon space, obtaining Radon data for the fine and coarse resolution points, and inverting the Radon data to provide the multi-resolution image data;
    said calculating and obtaining substeps using weighted integration; and
    displaying an image of the region of interest based on said multi-resolution image data, said image having a higher resolution relative to the spotlight region than outside of the spotlight region.

7. The method of claim 6 wherein the step of acquiring multi-resolution sensed data uses further a multi-resolution array detector with each of said second detector elements having a larger surface area than a surface area of each of said first detector elements.

* * * * *